(12) United States Patent
Ranganathan

(10) Patent No.: US 9,980,988 B2
(45) Date of Patent: *May 29, 2018

(54) COMPOSITIONS AND METHODS FOR AUGMENTING KIDNEY FUNCTION

(75) Inventor: Natarajan Ranganathan, Broomall, PA (US)

(73) Assignee: KIBOW BIOTECH, INC., Newton Square, PA (US)

( * ) Notice: Subject to any disclaimer, the term of this patent is extended or adjusted under 35 U.S.C. 154(b) by 1104 days.

This patent is subject to a terminal disclaimer.

(21) Appl. No.: 12/890,951

(22) Filed: Sep. 27, 2010

(65) Prior Publication Data

US 2011/0097307 A1   Apr. 28, 2011

Related U.S. Application Data

(63) Continuation-in-part of application No. 12/407,201, filed on Mar. 19, 2009, which is a continuation of application No. 10/936,262, filed on Sep. 8, 2004, which is a continuation-in-part of application No. PCT/US02/07554, filed on Mar. 13, 2002.

(51) Int. Cl.

| | |
|---|---|
| *A61K 35/744* | (2015.01) |
| *A61K 31/702* | (2006.01) |
| *A61K 35/74* | (2015.01) |
| *A61K 45/06* | (2006.01) |
| *A61K 35/745* | (2015.01) |
| *A61K 35/747* | (2015.01) |
| *A23L 33/135* | (2016.01) |
| *A23L 33/17* | (2016.01) |

(52) U.S. Cl.
CPC .......... *A61K 35/744* (2013.01); *A23L 33/135* (2016.08); *A23L 33/17* (2016.08); *A61K 31/702* (2013.01); *A61K 35/74* (2013.01); *A61K 35/745* (2013.01); *A61K 35/747* (2013.01); *A61K 45/06* (2013.01)

(58) Field of Classification Search
CPC ...... A61K 35/744; A61K 35/20; A23L 1/3014
USPC .............................. 424/93.44, 535
See application file for complete search history.

(56) References Cited

U.S. PATENT DOCUMENTS

| | | | |
|---|---|---|---|
| 4,022,883 A | 5/1977 | Setala | |
| 4,218,541 A | 8/1980 | Ackerman | |
| 4,569,846 A * | 2/1986 | Ohzeki et al. | 426/40 |
| 4,970,153 A | 11/1990 | Kobashi et al. | |
| 5,116,737 A | 5/1992 | McCoy | |
| 5,258,181 A | 11/1993 | Cregier et al. | |
| 5,716,615 A | 2/1998 | Vesely et al. | |
| 5,952,021 A | 9/1999 | Santus | |
| 6,319,895 B1 * | 11/2001 | Tomita et al. | 424/464 |
| 2002/0090416 A1 * | 7/2002 | Connolly | 426/2 |
| 2003/0077255 A1 * | 4/2003 | Sabharwal | 424/93.4 |
| 2007/0166433 A1 * | 7/2007 | Peneva et al. | 426/43 |
| 2007/0207187 A1 * | 9/2007 | Yajima et al. | 424/439 |

FOREIGN PATENT DOCUMENTS

| | | |
|---|---|---|
| EP | 1145643 A1 | 10/2001 |
| EP | 11832930.9 | 9/2015 |
| WO | WO 99/49877 | 10/1999 |
| WO | WO 00/71138 A2 | 11/2000 |
| WO | WO 00/71139 A2 | 11/2000 |
| WO | WO 00/74689 A1 | 12/2000 |
| WO | WO 00/74712 A2 | 12/2000 |
| WO | WO 05/032591 | 4/2005 |
| WO | WO 2008/076975 A1 * | 6/2008 |

OTHER PUBLICATIONS

Gibson, G. and Roberfroid, M. B. "Dietary Modulation of the Human Colonic Microbiota: Introducing the Concept of Prebiotics" the Journal of Nutrition 1995 125:1401-1412.
Office action from U.S. Appl. No. 12/407,201, dated Apr. 30, 2010, Ranganathan.
Office action from U.S. Appl. No. 12/407,201, dated May 27, 2010, Ranganathan.
Office action from U.S. Appl. No. 12/407,201, dated Oct. 12, 2010, Ranganathan.
Office action from U.S. Appl. No. 12/407,201, dated Feb. 17, 2011, Ranganathan.
Natarajan et al. "Probiotic Amelioration of Azotemia in $5/6^{th}$ Nephrectomized Sprague Dawley Rats" the Scientific World Journal 2005 5:652-660, XP055209289.

* cited by examiner

*Primary Examiner* — Susan Hoffman
(74) *Attorney, Agent, or Firm* — Licata & Tyrrell P.C.

(57) ABSTRACT

The present invention provides a nutritional food product composed of a prebiotic and an isolated protein for use in reducing elevated levels of nitrogenous waste products in the blood and ameliorating renal failure.

4 Claims, No Drawings

COMPOSITIONS AND METHODS FOR AUGMENTING KIDNEY FUNCTION

INTRODUCTION

This application is a continuation-in-part of U.S. Ser. No. 12/407,201 filed Mar. 19, 2009, now U.S. Pat. No. 8,257,693, which is a continuation of U.S. Ser. No. 10/936,262 filed Sep. 8, 2004, now abandoned, which is a continuation-in-part of U.S. Ser. No. PCT/US2002/007554 filed Mar. 13, 2002, each of which are incorporated herein in their entireties.

BACKGROUND OF THE INVENTION

One of the main functions of the normal, healthy kidney, besides its regulatory, endocrine, and metabolic functions, is the disposal of waste products. Any impairment of excretory function can lead to the accumulation of a variety of nitrogenous waste products including, urea, creatinine and uric acid. High concentrations of waste products in the blood stream can exacerbate renal failure and promote kidney stones. Moreover, nitrogenous solutes in the circulating blood promote osmotic diffusion into the lumen because of the concentration gradient across the intestinal wall. This diffusion mechanism led to the concept of oral sorbents to augment gut-based clearance of nitrogenous waste products. Sorbents or microbes have demonstrated their ability to remove various compounds and nitrogenous wastes within the large bowel.

Urea-specific sorbents such as synthetic polymers and modified polysaccharides have been evaluated for the removal of urea and other nitrogenous wastes via the gut. Other sorbents such as oxidized starch, activated charcoal, and carob flour have also been investigated for the in vivo elimination of uremic toxins with some success. Prakash & Chang ((1996) *Nature Medicine* 2:883-88) demonstrated that microencapsulated, genetically-engineered *E. coli* DH5 are effective in removing urea and ammonia in an in vitro system. The same researchers obtained similar results in oral administration of *E. coli* DH5 cells in a uremic rat animal model. Bliss et al. ((1996) *Am. J. Clin. Nutr.* 63:392-398) have demonstrated that supplemental gum arabic fiber increases fecal nitrogen excretion and lowers urea nitrogen concentration in chronic renal failure patients consuming a low protein diet. Reinhart et al. ((1998) *Rec. Adv. In Canine and Feline Nutr. Iams Nutrition Symposium Proceedings*. Vol. II:395-404) found that canine renal patients fed a diet containing a fermentable fiber blend improved clinical end-stage renal disease status, suggesting that specific nutritional alteration allows repartitioning of nitrogen excretion away from the kidney and into the feces by colonic fermentation or additional bacterial growth.

Prebiotic components are food ingredients that enhance the actions of probiotic components in the digestive tract. In this synergistic or relationship a probiotic component, such as *Bifidobacteria*, metabolizes undigested carbohydrates, such as dietary fibers, oligosaccharides, etc., to produce short-chain fatty acids such as acetate, propionate and butyrate. These short-chain fatty acids may promote intestinal cell growth, enhance water and mineral absorption, and prevent yeast, mold, and pathogenic bacterial growth. In addition, probiotic components may antagonize pathogens directly through production of antimicrobial and antibacterial compounds such as cytokines and butyric acid (De Vuyst and Vandamme. Antimicrobial potential of lactic acid bacteria. In: De Vuyst L, Vandamme E L, eds. Bacteriocins of lactic acid bacteria. Glasgow, United Kingdom: Blackie Academic and Professional; 1994:91-142; Dodd and Gasson. Bacteriocins of lactic acid bacteria. In: Gasson M J, de Vos W M, eds. Genetics and biotechnology of lactic acid bacteria. Glasgow, United Kingdom: Blackie Academic and Professional; 1994:211-51; Kailasapathy and Chin (2000) *Immunol. Cell. Biol.* 78(1):80-8), reduce gut pH by stimulating the lactic acid-producing microflora (Langhendries et al. (1995) *J. Pediatr. Gastroenterol. Nutr.* 21:177-81), compete for binding and receptor sites that pathogens occupy (Kailasapathy and Chin (2000) *Immunol. Cell. Biol.* 78(1): 80-8; Fujiwara et al., (1997) *Appl. Environ. Microbiol.* 63:506-12), improve immune function and stimulate immunomodulatory cells (Isolauri et al. (1991) *Pediatrics* 88:90-97; Isolauri et al. (1995) *Vaccine* 13:310-312; Rolfe (2000) *J. Nufr.* 130(2S):396S-402S), compete with pathogens for available nutrients and other growth factors (Rolfe (2000) *J. Nufr.* 130(2S):396S-402S), or produce lactase which aids in lactose digestion.

U.S. Pat. No. 4,022,883 discloses a method for alleviating uremic symptoms in persons suffering from renal failure comprising administering orally thereto an effective dosage of a cell mass of a non-pathogenic soil bacteria selected from the group consisting of an urea degrading bacterium, a creatine degrading bacterium, a creatinine degrading bacterium and an uric acid degrading bacterium wherein the urea degrading bacterium is a species of Serratia; the creatinine degrading bacterium is a non-fluorescent *Pseudomonas, Rhizobium, Agrobacterium, Corynebacterium ureafaciens, Arthrobacter ureafaciens, E. coli,* or *Pseudomonas aeruginosa*; and a uric acid degrading bacterium is *Bacillus subtilis,* a non-fluorescent *Pseudomonas, Bacillus fastidosus, Micrococcus dentrificans, Mycobacterium phlei, Aerobacter aerogenes*.

U.S. Pat. No. 4,218,541 teaches a method for converting urea to inocuous products. The method involves obtaining a culture of at least one microorganism selected from the group of Enterobacter agglomerans, Group D *Streptococcus, Bacilli,* and *Pseudomonad* or mixtures of said microorganisms and adding the culture to a composition containing urea.

U.S. Pat. No. 4,970,153 discloses a method of producing urease and more particularly a method of producing acid urease by the cultivation of *Lactobacillus fermentum* TK 1214. This patent further teaches the use of such acid urease or the decomposition of urea contained in fermentation food products.

U.S. Pat. No. 5,116,737 teaches a method for growing acid-producing bacterial cultures, such as diary cultures, wherein the culture is selected to contain a urease-producing strain of bacteria and the medium used for the culturing contains added urea. Urease-producing strains of *Streptococcus thermophilus* and *Bifidobacterium* are also disclosed.

U.S. Pat. No. 5,716,615 discloses a pharmaceutical composition containing several different bacteria including *Streptococcus thermophilus, Lactobacilli* and *Bifidobacteria* wherein the bacteria are present in the composition at a total concentration of $1 \times 10^{11}$ to $1 \times 10^{13}$ per gram. An excipient consisting of maltodextrin, microcrystalline cellulose, maize starch, levulose, lactose or dextrose is further taught. Methods of using the pharmaceutical composition are also disclosed which include treatment of a gastrointestinal disorder and hypercholesteremia or modulating a host's immune response.

SUMMARY OF THE INVENTION

The present invention is a protein-rich nutritional product composed of at least one prebiotic and at least one isolated edible protein. In one embodiment, the probiotic component is selected from the group of a *Lactobacillus, Bacillus, Streptococcus Bifidobacteria, Saccharomyces* or *Leuconostoc*. In other embodiment, the at least one isolated protein is selected from the group of whey proteins or isolates, concentrates or hydrolysates thereof; milk proteins or isolates, concentrates or hydrolysates thereof whey growth factor extract; glutamine peptide; egg albumen; soy proteins or isolates, concentrates or hydrolysates; or caseinates.

This nutritional composition can be in the form of a food product, dietary supplement, or medical food which, upon ingestion, will promote a healthy intestinal microenvironment, provide a source of protein, and assist in the elimination of nitrogenous waste products that can build up in concentration in the circulating blood. Increased concentrations of the wastes are known to exert a negative impact on an individual's physiology and contribute to a decreased sense of well-being and general malaise. Methods for removing nitrogenous waste products from the blood and ameliorating renal failure using the nutritional product of the invention are also provided.

DETAILED DESCRIPTION OF THE INVENTION

Nitrogenous waste products accumulating in the blood stream have detrimental affects on health. Removal of nitrogenous wastes by diverting them into the colon is a viable approach to decrease the negative impact that waste product accumulation has on an individual's physiology. The present invention combines the properties of a probiotic and edible protein into a product to both provide a source of protein and effectively reduce the blood concentration of nitrogenous waste products.

A probiotic component of the present invention refers to a mono or mixed culture of live or freeze-dried microorganisms which, when applied to man or animal, beneficially affects the host by improving the properties of the indigenous microflora, such as bifidobacterium organisms that metabolize undigested carbohydrates and are beneficial to an individual. Probiotic components of the present invention are selected for their ability to exert a beneficial effect on the host, survive transit through the intestinal tract, to adhere to intestinal epithelial cell lining, to produce of anti-microbial substances towards pathogens and/or to stabilize the intestinal microflora. Furthermore, a probiotic component should have a good shelf-life. Products of the present invention generally contain a large number of viable cells at the time of consumption, and are non-pathogenic and nontoxic. Examples of probiotic components include, but are not limited to, *Bifidobacterium* spp. (e.g., *bifidum, longum, infantis*), *Lactobacillus* spp. (e.g., *bulgaricus, acidophilus, lactis, helveticus, casei, plantarum, reuteri, delbrueckii, chamnosus, johnsonii, paracasei*), *Streptococcus* spp. (e.g., *thermophilus, diacetilactis, cremoris, durans, faecalis*), *Saccharomyces* spp. (e.g., *pombe, boulardii*), *Leuconostoc* spp. (e.g., *citrovorum, dextranicum*) and *Bacillus* sp. (e.g., *pasteurii*). In one embodiment, the probiotic component is composed of at least one, at least two, or at least three microorganisms from the genera *Bifidobacterium, Lactobacillus, Streptococcus, Saccharomyces, Leuconostoc* and *Bacillus*. In another embodiment, the probiotic component is composed of at least one microorganism from the genera *Bifidobacterium, Streptococcus* or *Lactobacillus*. In a further embodiment, the probiotic component is composed of at least two microorganisms from the genera *Bifidobacterium, Streptococcus* or *Lactobacillus*. In a particular embodiment, the probiotic component is composed of *Bifidobacterium longum, Streptococcus thermophilus* and *Lactobacillus acidophilus*.

Microorganisms also useful in the invention are those that have the ability, either through natural selection or by genetic manipulation, to catabolize various nitrogenous compounds (e.g., urea, creatinine, uric acid and ammonia) by expressing or overexpressing one or more cognate catabolic enzymes. Exemplary microorganisms are those having an elevated level of urease or creatininase secretion.

A microorganism exhibiting elevated levels of catabolic enzyme secretion can be selected or trained by exposing a selected microorganism on increasing amounts of the metabolite of interest (e.g., urea, creatinine, uric acid and ammonia). For example, it has been found that a standard strain of Streptococcus thermophilus can be trained to express elevated levels of urease by sequential passage of the strain on increasing amounts of urea, e.g., a single colony growing on 0.5% urea is selected and applied to medium containing 1.0% urea, a single colony growing on 1.0% urea is selected and applied to medium containing 2.0% urea, etc. Using such a method, a S. thermophilus strain having the ability to grow on 5% urea was isolated. This strain proliferated in artificial intestinal fluid (AIF, US Pharmacopeia) in the pH range of 5.5 to 7.5, characteristic of the colon environment; used urea as a sole nitrogen source; and catabolized urea in the presence of other nitrogen sources. It was found that urea hydrolysis was growth- and pH-dependent and that urea concentrations could be reduced by this strain from 300 mg/dL to 20 mg/dL within 24 hours at pH 6.3 when inoculated in AIF at an initial density of $10^9$ cfu/mL. Moreover, this strain survived 3 hours in acidic pH 3.0 with only a one-log loss in cfu and was able to pass through bile. In addition, this strain did not appear to exhibit any resistance to eight commonly used antibiotics. Therefore, these data indicate that a specifically selected or trained bacterial isolate can be used as a urea-targeted component in a product of the present invention.

Elevated levels of secretion can also be obtained by overexpressing the gene of interest (e.g., via multiple copies or a promoter driving high levels of expression) in a prokaryotic microorganism of interest such as *Bifidobacterium, Lactobacillus, Streptococcus, Leuconostoc* or *Bacillus*, or a eukaryotic microorganism such as *Saccharomyces*. The gene of interest can be under the regulatory control of an inducible or constitutive promoter. Promoters for use in recombinant prokaryotic expression vectors are well-established in the art and can include the beta-lactamase (penicillinase) and lactose promoter systems (Chang et al. (1978) *Nature* 275: 615; Goeddel et al. (1979), *Nature* 281:544), a tryptophan (trp) promoter system (Goeddel et al. (1980) *Nucleic Acids Res.* 8:4057; EPO App. Publ. No. 36,776) and the tac promoter (De Boer et al. (1983) *Proc. Natl. Acad. Sci. USA* 80:21). While these are commonly used promoters which are commercially available, one of skill in the art can appreciate that any other suitable microbial promoter can be used as well. Nucleic acid sequences encoding suitable prokaryotic promoters have been published thereby enabling one of skill in the art to readily isolate these promoters (e.g., by standard cloning or PCR methodologies) for cloning into plasmid or viral vectors (Siebenlist et al. (1980) *Cell* 20:269). The promoter and Shine-Dalgarno sequence (for prokaryotic host expression) are operably-linked to the DNA encoding the gene of interest, i.e., they are positioned so as to promote transcription of the messenger RNA from the DNA, and subsequently introduced into a suitable host cell.

Eukaryotic microbes such as yeast cultures can also be transformed with suitable protein-encoding vectors. See e.g., U.S. Pat. No. 4,745,057. *Saccharomyces cerevisiae* is the most commonly used among lower eukaryotic host microorganisms, although a number of other strains are commonly available. Yeast vectors can contain an origin of replication from the 2 micron yeast plasmid or an autonomously replicating sequence (ARS), a promoter, DNA encoding the desired protein, sequences for polyadenylation and transcription termination, and a gene encoding for a selectable marker. An exemplary plasmid is YRp7, (Stinchcomb et al. (1979) *Nature* 282:39; Kingsman et al. (1979) *Gene* 7:141; Tschemper et al. (1980) *Gene* 10:157). This plasmid contains the trp1 gene, which provides a selection marker for a mutant strain of yeast lacking the ability to grow in tryptophan, for example ATCC No. 44076 or PEP4-1 (Jones (1977) *Genetics* 85:12). The presence of the trp1 lesion in the yeast host cell genome then provides an effective environment for detecting transformation by growth in the absence of tryptophan.

Suitable promoting sequences in yeast vectors include the promoters for metallothionein, 3-phospho-glycerate kinase (Hitzeman et al. (1980) *J. Biol. Chem.* 255:2073) or other glycolytic enzymes (Hess et al. (1968) *J. Adv. Enzyme Reg.* 7:149; Holland et al. (1978) *Biochemistry* 17:4900), such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Suitable vectors and promoters for use in yeast expression are commercially available and further described in Hitzeman et al., EP 73,657.

As will be understood by those of skill in the art, expression vectors containing polynucleotides which encode a degradative enzyme of interest, e.g., a urease or creatininase, can be designed to contain signal sequences which direct secretion of enzyme of interest through a prokaryotic or eukaryotic cell membrane. Such signal sequences are well-established in the art and can be taken from other enzymes/proteins known to be secreted into the extracellular environment.

Transforming the microorganisms as defined herein, describes a process by which exogenous DNA is introduced into and changes a recipient cell. It can occur under natural or artificial conditions using various methods well-known in the art. Transformation can rely on any known method for the insertion of foreign nucleic acid sequences into a prokaryotic or eukaryotic host cell. The method is selected based on the type of host cell being transformed and can include, but is not limited to, viral infection, electroporation, heat shock, lipofection, and particle bombardment. Such "transformed" cells include stably-transformed cells in which the inserted DNA is capable of replication either as an autonomously replicating plasmid or as part of the host chromosome. This also includes cells which transiently express the inserted DNA or RNA for limited periods of time.

As will be appreciated by the skilled artisan, a microorganism can also be exposed to a mutagen to cause changes in the genetic structure of the organism so that it expresses elevated levels of a catabolic enzyme of interest.

Transformed or mutagenized strains are subsequently selected for the ability to grow in the presence of the metabolite which is degraded by the catabolic enzyme of interest. By way of example, a strain transformed with nucleic acid sequences encoding a urease is selected for high levels of urease secretion by growing said strain on high levels of urea. Levels of urease secretion can also be detected using standard enzymatic assays. As disclosed herein, the strain can be sequentially subcultured on increasing levels of urea to further enhance urease secretion. One embodiment of the present invention provides a urease-secreting strain of *Bacillus pasteurii*, *Streptococcus thermophilus* or *Saccharomyces pombe*. In another embodiment, a urease-secreting strain is at least one of the microorganisms of a probiotic component composed of at least two or at least three microorganisms. In a further embodiment, a urease-secreting strain is at least two of the microorganisms of a probiotic component composed of at least three microorganisms.

The probiotics according to the invention can be obtained by fermentation and can be stored after fermentation and before addition to the composition of the present invention for a time and at a temperature that prevents substantial loss of probiotic cfu. For example, the probiotic component can be fermented until a final concentration of $10^6$ to $5 \times 10^{10}$, or $10^7$ to $10^{10}$, or $10^8$ to $10^9$ cfu per mL of fermented medium is achieved.

When the probiotic component is a mono culture, said mono culture is 100% of the probiotic component. When the probiotic component is composed of at least two microorganisms, each microorganism can be 10, 15, 20, 30, 40, 50, 60, 70, 80, or 90% of the probiotic component, wherein the total of all microorganisms is 100%. An exemplary probiotic component is composed of about 10-15% *L. acidophilus*, about 10-15% *B. longum* and about 70-80% *S. thermophilus* (e.g., a ratio of approximately 1:1:8, respectively).

The probiotic component or urease-secreting microorganism is included at a concentration of $10^8$ cfu/mL, $10^9$ cfu/mL, $10^{10}$ cfu/mL, $10^{11}$ cfu/mL, or $10^{12}$ cfu/mL when added as a liquid or $10^8$ cfu/g, $10^9$ cfu/g, $10^{10}$ cfu/g, $10^{11}$ cfu/g, or $10^{12}$ cfu/g when added as a freeze-dried powder. In one embodiment, the probiotic component is about 20% to about 70% of the total product weight, In particular embodiments, the probiotic component is about 50% of the total product weight.

Edible nutritional proteins and their derivatives provide specific benefits, in particular in subjects with stage 5 renal failure who exhibit significant protein loss. For example, whey protein isolate (WPI) and milk protein isolate (MPI) have been shown to effectively provide a gain in lean muscle mass. WPI is high in branched-chain amino acids. MPI is primarily casein, shown effective in promoting muscle growth. Egg protein (albumen) also is high in amino acid content. Whey protein hydrosylate (WPH) has been linked to improved nitrogen retention and growth in rats. Accordingly, in particular embodiments, the edible protein of the invention is a whey protein or isolate, concentrate or hydrolysate thereof; milk protein or isolate, concentrate or hydrolysate thereof; whey growth factor extract; glutamine peptide; egg albumen; soy protein or isolate, concentrate or hydrolysate; or caseinate. In the instant composition, the protein is added as an ingredient per se and is not sourced from other ingredients such as peanut pieces. In this respect, the protein is isolated, i.e., obtained from its natural source as an extract or purified protein (e.g., greater than 90% homogenous to the protein with fats and carbohydrates removed).

When the protein is a single edible protein, said protein is 100% of the protein component. When the protein component is composed of two or more protein, each protein can be 5, 10, 15, 20, 30, 40, 50, 60, 70, 80, or 90% of the protein component, wherein the protein component total is 100%.

The amount of protein component added to the composition of the invention is provided in the range of 10 to 50 grams per serving. In one embodiment, the protein component is not less than 10 grams and not more than 100 grams per serving. In one embodiment, the protein component is about 20% to about 70% of the total product weight, In particular embodiments, the protein component is about 50% of the total product weight. When the product further includes addition additives, the percent of the protein can be decreased to accommodate the additional additive.

In some embodiments, the composition of the invention further includes a prebiotic component. A prebiotic refers to a non-digestive food that beneficially affects the host by selectively stimulating the growth and/or activity of one or more non-pathogenic bacteria in the colon. Prebiotic components of the present invention are considered to have anti-carcinogenic, anti-microbial, hypolipidemic and glucose modulatory activities. They can also improve mineral absorption and balance. Furthermore, bacteria belonging to the *Bifidobacterium* and *Lactobacillus* families are stimulated by the presence of the prebiotic component and proliferate. Pharmacokinetically, the prebiotic components reach the colon largely intact. An exemplary prebiotic component includes, but is not limited to, an oligosaccharide such as fructo-oligosaccharide or inulin, isomaltose oligosaccharide, trans-galacto-oligosaccharide, xylo-oligosaccharide, or soy-oligosaccharide; a pyrodextrin such as arabinogalactan, lactitol, lactosucrose, or lactulose; or a fiber source such as oat gum, pea fiber, apple fiber, pectin, guar gum, psyllium husks, glucomannan or guar gum hydrolysate (BENEFIBER, Novartis Pharmaceuticals). In one embodiment, the prebiotic component is composed of at least one, at least two, or at least three non-digestive foods (e.g., oligosaccharides, pyrodextrins or a fiber source). In another embodiment, an oligosaccharide is at least one of the non-digestive foods of a prebiotic component composed of at least two or at least three non-digestive foods. In yet another embodiment, a fiber source is at least one of the non-digestive foods of a prebiotic component composed of at least two or at least three non-digestive foods. In a further embodiment, a fiber source is at least two of the non-digestive foods of a prebiotic component composed of at least three non-digestive foods. In a still further embodiment, the prebiotic component is composed of at least one of the following non-digestive foods of lactulose, psyllium husks and guar gum hydrolysate. In particular embodiments, the prebiotic component is composed of lactulose, psyllium husks and guar gum hydrolysate.

A nutritional product combining the beneficial properties of a probiotic and edible food protein can include a food product, dietary supplement, comestible medical food or pharmaceutical product. The ingestion of said product provides both a protein source and reduces the blood concentration of nitrogenous waste products that accumulate in the circulating blood stream. These waste products of the present invention can be of an endogenous origin such as normal or abnormal metabolic routes or bacterial putrefaction. Furthermore, the waste products can be of an exogenous origin as in dietary intake of proteins and amino acids. Furthermore, repeated ingestion of the product will have a highly beneficial effect upon the intestinal microflora by localization and colonization in the large intestine of microbes known to promote a healthy intestinal microenvironment.

A product of the present invention can take the form of a food product including, but is not limited to, a health bar, health drink, yogurt, dahi, ice cream, frozen yogurt or other frozen food product. In addition to containing protein and probiotic components, the product of the present invention can further containing various fillers or additives.

Optional additives of the present composition include, without limitation, pharmaceutical excipients such as magnesium stearate, talc, starch, sugars, fats, antioxidants, amino acids, proteins, nucleic acids, electrolytes, vitamins, derivatives thereof or combinations thereof. In one embodiment, an additive of the product is carob flour, for example, locust bean gum. In another embodiment, an additive is a mushroom extract from Agaricus bisporus. In particular embodiments, a gel cap contains fillers such as magnesium stearate, talc and starch.

Further, to increase the palatability of a food product containing a protein and probiotic, it may be desirable to add flavors, sweetening agents, binders or bulking agents.

Flavors which can optionally be added to the present compositions are those well-known in the art. Examples include, but are not limited to, synthetic flavor oils, and/or oils from plants leaves, flowers, fruits and so forth, and combinations thereof are useful. Examples of flavor oils include, but are not limited to, spearmint oil, peppermint oil, cinnamon oil, and oil of wintergreen (methylsalicylate). Also useful are artificial, natural or synthetic fruit flavors such as citrus oils including lemon, orange, grape, lime, and grapefruit, and fruit essences including apple, strawberry, cherry, pineapple and so forth.

Sweetening agents can be selected from a wide range of materials such as water-soluble sweetening agents, water-soluble artificial sweeteners, and dipeptide-based sweeteners, including salts thereof and mixtures thereof, without limitation.

Binders can be selected from a wide range of materials such as hydroxypropylmethylcellulose, ethylcellulose, or other suitable cellulose derivatives, povidone, acrylic and methacrylic acid co-polymers, pharmaceutical glaze, gums (e.g., gum tragacanth), milk derivatives (e.g., whey), starches (e.g., corn starch) or gelatin, and derivatives, as well as other conventional binders well-known to persons skilled in the art. Examples of bulking substances include, but are not limited to, sugar, lactose, gelatin, starch, and silicon dioxide.

When the above-mentioned additives are included in the product of the present invention, they are generally less than 15% of the total product weight. In particular embodiments, they are less than 5 to 10% of the total product weight.

Depending on whether the product is to be consumed by an adult human, child or animal (e.g., companion animal or livestock), it can be produced in various sizes and with various ingredients suitable for the intended recipient. Further, because the probiotic and protein components of the present invention are generally recognized as safe, they can be consumed one, two or three times daily or more.

The present invention also relates to a method for removing nitrogenous waste products from the blood of an individual with elevated levels of nitrogen-containing waste products. The method involves administering an effective amount of a product of the present invention so that the levels of nitrogenous waste products in the blood are decreased or reduced, desirably to a normal range. For example, normal levels of creatinine in the blood are in the range of 0.6-1.2 mg/dL, whereas normal blood urea nitrogen (BUN) levels range from 7-18 mg/dL and normal uric acid levels in males and females is in the range of 2.1 to 8.5 mg/dL and 2.0 to 7.0 mg/dL, respectively. Further, a BUN/creatinine ratio of 5-35 is indicative of normal levels of nitrogenous waste products in the blood. As one of skill in the art can appreciate, means for determining the levels of nitrogenous wastes are well-known to the skilled laboratory clinician.

As products of the present invention can reduce the levels of nitrogenous waste products in the blood of a mammal with chronic renal failure, these compositions are useful in a method for ameliorating renal failure. The method involves administering a product of the present invention to a subject having or at risk of having renal failure. Subjects having or at risk of having renal failure include those with diabetic nephropathy, hypertensive nephrosclerosis, glomerulonephritis, interstitial nephritis, or polycystic kidney disease wherein nephron function is impaired thereby decreasing glomerular filtration rate. Desirably, an effective amount of a product for ameliorating renal failure is an amount sufficient to effect beneficial or desired results, including clinical results, and, as such, an effective amount of a product is one which results in the alleviation or amelioration of one or more symptoms associated with renal failure (e.g., a build up of uremic solutes), diminishment of extent of disease, stabilized (i.e., not worsening) state of disease by supporting healthy bowel function, delay or slowing of disease progression, or amelioration or palliation of the disease state. Amelioration can also mean prolonging survival as compared to expected survival if not receiving treatment. In particular embodiments, the instant composition is administered to a subject with renal failure and a protein deficiency.

It is further contemplated that compositions of the present invention containing proteins and probiotics may have further utility in the providing energy and overall health and well-being in subjects undergoing cancer therapy.

EXAMPLE 1

Yogurt Food Product

Yogurt or frozen yogurt can be prepared from one gallon of commercially available whole, homogenized, pasteurized milk which is heated to boiling and quickly allowed to cool to approximately 45° C. To this is added approximately one ounce of yogurt starter culture containing lactic acid bacteria of the genus *Lactobacillus, Streptococcus, Bacillus* or *Bifidobacteria*. The mixture is mixed well and allowed to ferment at 37° C. for 10 to 12 hours. One or more proteins, prebiotics, whole fruit additives, flavoring, sweetening agents, binders, or other additives can be combined and added to the yogurt to obtain a product of desired consistency or to suit the palette of the prospective consumer. In one embodiment of the present invention, a food product comprises components to meet the special dietary needs of individuals with renal insufficiency.

EXAMPLE 2

Health Bar

Health bars can be prepared by combining various excipients, such as binders, additives, flavorings, colorants and the like, along with the probiotic (e.g., *Lactobacillus, Streptococcus, Bacillus* or *Bifidobacteria*) and protein such as soy protein isolate, and mixing to a plastic mass consistency. The mass is then either extruded or molded to form "candy bar" shapes that are then dried or allowed to solidify to form the final product.

EXAMPLE 3

Medical Food

A medical food can be prepared by combining rolled oats, dehydrated apples, honey, inulin, carob flour, cinnamon, sugar, vanilla extract, and protein such as whey protein isolate, and lyophilized cultures of *L. acidophilus* and or *L. fermentum*, a *Bifidobacteria*, and *Streptococcus thermophiles* ($10^8$-$10^{10}$ cfu each). These ingredients are mixed in appropriate proportions with a prebiotic and formed into a rectangular bar approximately 12.5 to 15 centimeters in length, 3 to 4 centimeters in width and 1 centimeter in height and placed into a sterile vacuum oven for 12 to 24 hours to obtain an edible food product of the desired consistency.

EXAMPLE 4

Minipig Model of Chronic Uremia

The effects of a composition of the present invention in the form of a gel cap product or formulation admixed with the pig chow were tested using an established model of chronic uremia (mild to moderate) in the Gottingen strain of miniature swine (Willis, et al. (1997) *J. Endourol.* 11(1):27-32). At sexual maturity (3 months of age) these pigs weigh 8-11 kg, and are about half the size of all other strains of minipigs. The pigs grow slowly and double their body weight in about 6 months.

In this uremic model, ⅚ of the renal mass is removed through bilateral flank incisions (McKenna, et al. (1992) *J. Urol.* 148(2 Pt 2):756-9). One kidney is entirely removed, and both poles of the contra lateral kidney are removed with the aid of electro-cautery (for scoring the renal capsule and about 2 mm of parenchyma), surgical staples, and Gel foam sutured over the exposed parenchyma of the remnant. The contra lateral kidney is removed during the same surgical procedure by gross dissection and ligation and section of the renal artery and vein and ureter. The pigs used in this analysis characteristically experienced a large, acute elevation of creatinine and Blood Urea Nitrogen (BUN) concentrations in plasma; followed by a decline over 1-2 weeks to values that stabilized well above baseline. These pigs maintained their appetite and stable uremia for 3-6 months, maintained or gained body weight, and behaved no differently than normal control pigs. Hematocrits declined slowly as the uremia progressed and hemoglobin concentrations also declined over time. After the surgery, the pigs were allowed to recover for 3-4 weeks prior to administering the compositions.

Using this model, several different blinded formulations in the form of gel caps or admixed with the pig chow were tested as gut-based therapy for uremia. Formulations administered with the pig chow did not demonstrate any significant differences either in BUN or creatinine values. However, ⅚$^{th}$ nephrectomized mini pigs (n=6) given a formulation containing four microbial strains (*L. acidophilus, L. bulgaricus, B. longum* and *S. thermophilus*; $10\times10^9$ CFU/gel cap) exhibited continued body weight gains of approximately 31% and decreased BUN and creatinine levels of approximately 13% each. Similarly, two ⅚$^{th}$ nephrectomized mini pigs given a formulation containing three microbial strains (*L. acidophilus, B. longum* and *S. thermophilus*; $10\times10^{10}$ CFU/gel cap) also showed a decrease in BUN (average 21%) and creatinine (average 29%) levels although the body weight of one mini pig increased (6%) and the other decreased (20%). Additional formulations were tested in the form of gel caps or admixed with food and in general the results indicated that oral treatment with a probiotic formulation effectively and significantly reduced plasma creatinine concentrations by 22.5±8.5% in a stable porcine model of chronic renal failure. Small sample size may have prevented detection of corresponding reductions in BUN and elevation of hematocrit.

EXAMPLE 5

Animal Dosing

Table 1 provides a suitable approximate serving dosage of a nutritional product for administration to an animal such as a companion animal.

TABLE 1

| Weight pounds (Kg) | Morning Dose | Evening Dose |
|---|---|---|
| Less than 2.2 lbs (<1 Kg) | 1 | 0 |
| 2.2-4.4 lbs (1-2 Kg) | 1 | 1 |
| 4.4-8.8 lbs (2-4 Kg) | 2 | 1 |
| 8.8-17.6 lbs (4-8 Kg) | 2 | 1-2 |
| 17.6-35.2 lbs (8-16 Kg) | 2 | 2 |
| 35.2-70.4 lbs (16-32 Kg) | 2-3 | 2-3 |
| More than 70.4 lbs (>32 Kg) | 3 | 3 |

EXAMPLE 6

Urease-secreting Strains of *Streptococcus thermophilus*

This example discloses the isolation and selection of a high level urease-secreting strain of *Streptococcus thermophilus*. Three isolates of gram-positive, lactic acid-producing non-pathogenic cocci of *Streptococcus thermophilus* were isolated from various sources and designated KB4, KB19, and KB25. KB4 was isolated from a probiotic product, KB19 was isolated from a commercial yogurt product and KB25 from Dahi yogurt (from India).

Growth rates and urea hydrolysis of these bacteria in the intestinal pH range (pH 5.5, 6.3 and 7.5) were determined by transferring exponentially growing cultures of KB19, KB4 and KB25 into modified Artificial Intestinal Fluid M2 (AIF, US Pharmacopeia) supplemented with 100 mg/dL filter-sterilized urea, 100 µM $NiCl_2$, 10% MRS broth, dextrose to final concentration of 1%, and 0.3% yeast extract, wherein the initial cell density was $10^9$ cfu/mL. Pancreatin was omitted from the recipe to allow the evaluation of bacterial growth by direct OD600 nm measurement. Urea concentration in the supernatants (% of control) and growth (OD600 nm) were measured every 4 hours.

Concentration of urea in the supernatants of bacterial cultures was measured using the protocol and standards supplied with the Blood Urea Nitrogen Reagent Kit (535, SIGMA, St. Louis, Mo.). Urea hydrolysis was monitored by comparing urea-nitrogen concentrations in bacterial supernatants to appropriate control medium incubated in the same conditions and expressed as percent of control. Four to nine independent experiments were conducted and Student t-test was used for statistical analysis.

Under similar assay conditions, exponentially growing cultures of KB19, KB4 and KB25 were inoculated into AIF M2, pH 6.3, supplemented with 100 mg/dL urea and with or without 100 µM $NiCl_2$ at initial cell density of $10^9$ cfu/mL to determine whether the growth and rates of urea hydrolysis by these strains was dependent on the additional Ni++. Urea concentration in the supernatants as a % of control and growth (OD600 nm) were measured every 4 hours. Four to nine independent experiments were conducted and Student t-test was used for statistical analysis. Similarly, it was determined whether the growth and rate of urea hydrolysis of these strains was dependent on urea concentration. Under similar growth conditions exponentially growing cultures of KB19, KB4 and KB25 were inoculated into AIF M2, pH 6.3, supplemented with 100 µM $NiCl_2$ and 100, 200, or 300 mg/dL urea. Urea concentration in the supernatants as a % of the control and growth (OD600 nm) were measured every 4 hours. Four to nine independent experiments were conducted and Student t-test was used for statistical analysis. The survivability of these KB19, KB4 and KB25 was determined in artificial gastric juice in the presence and absence of urea and dextrose. The average loss in viable cell count after exposure to artificial gastric juice (logs cfu/mL) is shown in Table 2.

TABLE 2

| PH/Additive | KB19 | KB4 | KB25 |
|---|---|---|---|
| 1.4 | 7 | 7 | 7 |
| 2.0 | 7 | 7 | 7 |
| 2.5 | 3 | 4 | 4 |
| 2.5/Urea | 3 | 4 | 4 |
| 2.5/Dextrose | 3 | 3 | 3 |
| 2.5/Urea + Dextrose | 3 | 3 | 3 |
| 3.0 | 2 | 2 | 3 |
| 3.0/Urea | 2 | 3 | 3 |
| 3.0/Dextrose | 1 | 2 | 3 |
| 3.0/Urea + Dextrose | 1 | 2 | 2 |

Initial cell density was $10^7$ cfu/mL. Urea and dextrose concentrations were 10 mg/mL and 1%, respectively.

Further it was determined whether the nutrient composition and availablility had an affect on growth and urea hydrolysis by KB19, KB4, and KB25. Each strain was grown for 24 hours at 37° C. and pH 6.0 in the presence or absence of 100 mg/dL of urea and combinations of nitrogen and carbon sources.

Further analysis of *S. thermophilus* KB19 indicated that this strain could survive a 3 hour exposure to gastric juice, pH 3.0, followed by a 3 hour exposure to 0.3% oxgal, pH 6.0, with only 1 log loss in viability. Remaining viable cells were able to proliferate in AIF M2, pH 6.0, supplemented with 230 mg/dL urea and completely hydrolyzed the urea within less than 18 hours (n=4). All test solutions were supplemented with 230 mg/dL urea and 1% dextrose. Collectively, these analyses indicated that all three strains studied proliferated in the fed state AIF medium in the pH range from 5.5 to 7.5, characteristic of colon environment; they could all use urea as a sole nitrogen source; and they each catabolized urea in the presence of other nitrogen sources. Urea hydrolysis was growth and pH dependent. Under the conditions tested, the rate of urea hydrolysis was strain-dependent in tests of pH stability: KB19=KB25>KB4; Ni requirement: KB25>KB19>KB4; urea hydrolysis for over 300 mg/dL: KB19=KB25>KB4; and specific nutrients: KB19>KB25>KB4. Further, there was strain-dependent results relating to survivability, wherein in tests of gastric juice stability: KB19>KB4>KB25; and bile stability: KB19>KB4>KB25.

In view of the desirable traits exhibited by *S. thermophilus* KB19 it was further determined, using a disc-diffusion test, that K19 was sensitive to Spectinomycin (100 μg), Kanamycin (30 μg), Chloramphenicol (30 μg), Spectinomycin (100 μg), Penicillin (10 IU), Carbenicillin (100 μg), Doxycycline (30 μg), and neomycin (30μg). To further enhance the levels of urease secreted by strain K19, this strain was trained on increasing levels of urea as described herein.

What is claimed is:

1. A protein-rich nutritional product comprising
   (a) at least one probiotic component comprising *Streptococcus*,
   (b) at least one flavor, sweetening agent, binder or bulking agent, and
   (c) at least one isolated edible protein,
   wherein the nutritional product comprises a health bar, medical bar, health drink, yogurt, or frozen food product and wherein said isolated edible protein is in the range of 10 grams to 100 grams per serving, is 20 to 70% of the total product weight, and comprises milk protein hydrolysate and said probiotic is 20 to 70% of the total product weight.

2. A method for removing nitrogenous waste products from the blood comprising administering to a subject in need thereof an effective amount of a nutritional product of claim 1 thereby removing nitrogenous waste products from the blood of the subject.

3. A method for ameliorating renal failure comprising administering to a subject in need thereof an effective amount of the nutritional product of claim 1 thereby ameliorating renal failure.

4. The method of claim 3, wherein the subject has a protein deficiency.

* * * * *